United States Patent [19]

Major et al.

[11] Patent Number: 5,753,491
[45] Date of Patent: May 19, 1998

[54] USE OF NEURO-DERIVED FETAL CELL LINES FOR TRANSPLANTATION THERAPY

[76] Inventors: Eugene O. Major, 2919 Elmsmead Ct., Oakton, Va. 22124; Carlo S. Tornatore, 4315 Clagett Rd, University Park, Md. 20782; Gal Yadid, 2 Ha'Negev Street, Kfar Saba, Israel, 44505

[21] Appl. No.: 467,958

[22] Filed: Jun. 6, 1995

Related U.S. Application Data

[63] Continuation-in-part of Ser. No. 46,527, Apr. 13, 1993, abandoned.

[51] Int. Cl.$^6$ .............................. A61K 48/00; C12N 5/00; C12N 15/00
[52] U.S. Cl. ........................ 435/240.2; 435/172.3; 435/240.1; 435/320.1; 435/240.25; 514/44; 424/93.21
[58] Field of Search .................. 514/44, 48, 2; 800/2; 435/172.3, 320.1, 240.2, 240.25, 948, 235, 236, 240.1

[56] References Cited

U.S. PATENT DOCUMENTS

| | | | |
|---|---|---|---|
| 4,707,448 | 11/1987 | Major | 435/240.25 |
| 4,892,538 | 1/1990 | Acbischer et al. | 604/891.1 |
| 5,032,407 | 7/1991 | Wagner et al. | |
| 5,082,676 | 1/1992 | Gage et al. | 424/520 |

FOREIGN PATENT DOCUMENTS

| | | | |
|---|---|---|---|
| WO 89/09816 | 10/1989 | WIPO | C12N 5/00 |
| WO 90/05781 | 5/1990 | WIPO | F23G 5/20 |
| WO 91/06631 | 5/1991 | WIPO | 424/570 |

OTHER PUBLICATIONS

Bankiewicz et al., "The effect of fetal mesencephalon implants on primate MPTP-induced parkinsonism." *J. Neurosurg.* 72:231–244.

Bjorkland et al., "Reconstruction of the Nigrostriatal dopamine pathway by intracerebral Nigral transplants." *Brain Res.* 177:555–560 (1979).

Brundin, "Monitoring of cell viability in suspensions of embryonic CNS tissue and its use as a criterion for intracerebral graft survival." *Brain Res.*, 331:251–259 (1985).

Cattaneo, "Identifying and manipulating neuronal stem cells." *Trends in Neurosci.* 14:338–340 (1991).

Fisher et al., "Survival and function of intrastriatally grafted primary fibroblasts genetically modified to produce L-Dopa." *Neuron* 6:371–380 (1991).

Freed, "Substantia nigra grafts and Parkinson's disease: from animal experiments to human therapeutic trials." *Restor. Neurol. Neurosci.* 3:109–134 (1991).

Gage et al., "Intracerebral grating: a tool for the neurobiologist." *Neuron* 6:1–12 (1991).

Lendahl, "The use of cell lines in neurobiology." *Trends in Neurosci.* 13:132–137 (1990).

Lindvall et al., "Human fetal dopamine neurons surivive and improve motor function in Parkinson's disease." *Science* 247:574–577 (1990).

Lindvall et al., "Human fetal dopamine neurons grafted into the striatum in two patients with severe Parkinson's disease." *Arch. Neurol.* 46:615–631 (1989).

Major et al., "Establishment of a line of human fetal glial cells that supports JC virus multiplication." *Proc. Nat'l Acad. Sci. USA* 82: 1257–1262 (1985).

Noel et al., "A method for large-scale high-yield isolation of canine pancreatic Islets of Langerhans." *Metabolism* 31:184–187 (1992).

Plunkett et al., "Implantation of dispersed cells into primate brain." *J. Neurosurg.* 70:441–445 (1989).

Rosenberg et al., "Grafting genetically modified cells to the damaged brain: restorative effects of NGF expression." *Science* 242:1575–1577 (1988).

Sun et al., "Microencapsulated Hepatocytes: an in vitro and in vivo study." *Biomat., Art. Cells, Art Org.*, 15:483–496 (1987).

Taylor et al., "Improvements in MPTP–induced object retrieval deficits and behavioral deficits after fetal nigral grafting in monkeys." *Prog. Brain. Res.* 82:543–559. (1990.

Tornatore et al., "Implantation and survival of a human fetal astrocyte cell line in the basal ganglia of the non–human primate, rhesus monkey." *J. of Cellular Biochemistry, Abstract Supp.* 17E (Keystone Symposium on Gene Therapy, Apr. 12–18, 1993) New York, NY, p. 227, Abstract SZ 115.

Uchida et al., "Transfection of tyrosine hydroxlase CDNA into C6 cells. The synthesis and release of L–DOPA." *3–Biochem. Genetics* 110(11):207 (1989) Abstract No. 110:89851p.

Widner et al., "Biolateral fetal mesencephalic grafting in two patients with Parkinsonism induced by 1-methyl-4-phenyl-1, 2, 3, 6-tetrahydropyridine (MPTP)." *New Eng. J. Med.* 327:1556–1563 (1992).

Windner and Brundin, "Immunological aspects of grafting in the mammalian central nervous system. A review and speculative synthesis." *Brain Res. Rev.* 13:287–324 (1988).

Wolff et al., "Grafting fibroblasts genetically modified to produce L–dopa in a rat model of parkinson's disease." *Proc. Nat'l Acad. Sci. USA* 86:9011–9014 (1989).

Marshall, Science, 269, 1995, 1050–1055.
Culver et al., TIG, 10(5), 1994, 174–178.
Miller et al., Faseb J., 9, 190–199, 1995.
Hodgson, Exp. Opin. Ther. Pat., 5(5), 1995, 459–468.

*Primary Examiner*—Jacqueline M. Stone
*Assistant Examiner*—Andrew Milne

[57] ABSTRACT

The present invention generally relates to methods for treating a host by implanting genetically unrelated cells in the host. More particularly, the present invention provides human fetal neuro-derived cell lines, and methods of treating a host by implantation of these immortalized human fetal neuro-derived cells into the host.

23 Claims, 12 Drawing Sheets
(16 of 12 Drawings in Color)

FIG. I
FIG. 2

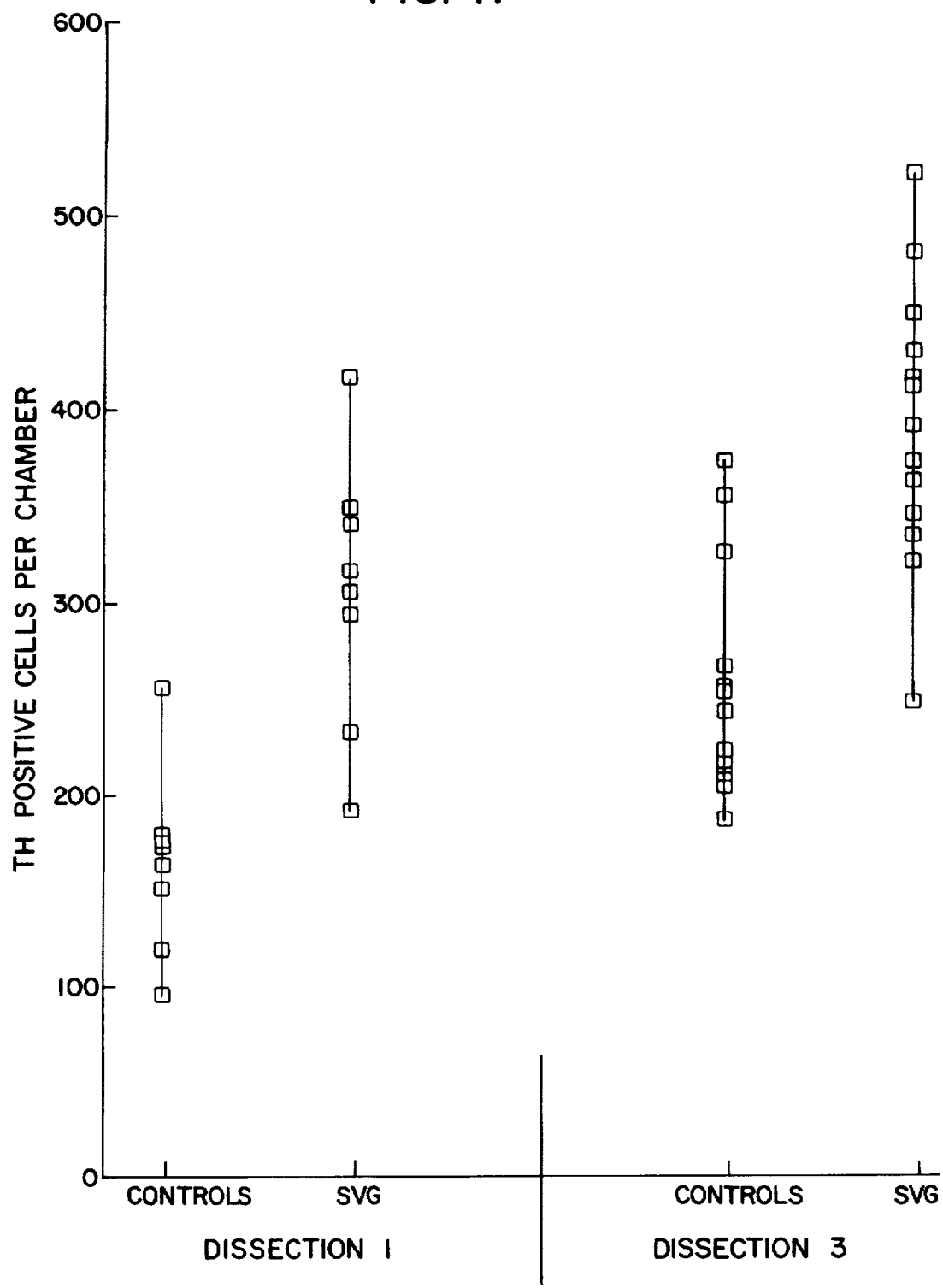

USE OF NEURO-DERIVED FETAL CELL LINES FOR TRANSPLANTATION THERAPY

This application is a continuation-in-part of U.S. patent application Ser. No. 08/046,527, filed Apr. 13, 1993, and incorporated herein by reference in its entirety for all purposes.

BACKGROUND OF THE INVENTION

The present invention relates generally to methods for treating a host by implanting genetically unrelated cells in the host. More particularly, the present invention provides immortalized human fetal neuro-derived cell lines, and methods of treating a host by implantation of these cell lines into the host or patient.

Organ transplantation has become a successful and widely practiced means of treating a variety of diseases. Cardiac, renal, and even liver transplants are almost routine in many medical centers. Unfortunately, disorders of many organs are not amenable to treatment with whole organ transplants. For example, lesions of the central nervous system may not be treated by whole organ transplants to replace damaged tissue.

Because replacement of injured tissue by whole organ transplant therapy is not possible for many diseases, or even for all patients having appropriate diseases, attempts have been made to develop methods of transplanting cells. Sun et al., *Biomat., Art. Cells, Art. Org.*, 15:483–496 (1987). Parenchymal lesions which result in a deficiency of a biologically active compound may be treated by transplanting isolated cells or cell clusters that secrete the biologically active compound. For example, diabetic animals have been successfully treated by implantation of islets of Langerhans separated from donor pancreases. Noel et al., *Metabolism*, 31:184 (1982).

Cell transplant therapy is particularly appealing for treatment of neurological diseases. Solid tissue transplantation is especially inappropriate for neurological diseases for several reasons. Open surgical exposure of the brain, as required for solid tissue transplantation, can cause irreparable damage to nervous system pathways resulting in clinical neurological deficits. Also, neurological function often depends on complex intercellular connections which can not be surgically established. Further, cells of the central nervous system are exquisitely sensitive to anoxia and nutrient deprivation. Rapid vascularization of solid tissue transplants is critical as cells in the interior of solid tissue transplants often lack sufficient perfusion to maintain viability. Stenevi et al., *Brain Res.*, 114:1–20 (1976).

One common neurological syndrome, Parkinsonism has been the object of attempts at cell transplant therapy. Bjorklund et al., *Brain Res.*, 177:555–560 (1979); Lindvall et al., *Science*, 247:574–577 (1990); Freed, *Restor. Neurol. Neurosci.*, 3:109–134 (1991). Parkinsonism is caused by a loss of dopamine-producing neurons in the substantia nigra of the basal ganglia. Burns et al., *N. Engl. J. Med.*, 312:1418–1421 (1985); Wolff et al., *Neurobiology*, 86:9011–9014 (1989). Parkinson's disease, a disease of unknown etiology which is characterized by the clinical manifestations of Parkinsonism, is caused idiopathic destruction of these dopamine-producing neurons. Parkinsonism may be caused by a variety of drugs, e.g., antipsychotic agents, or chemical agents, e.g., 1-methyl-4-phenyl-1,2,3,6-tetrahydropyridine. Burns et al., *Proc. Natl. Acad. Sci. USA*, 80:4546–4550 (1983) and Bankiewicz et al., *Life Sci.*, 39:7–16 (1986).

Attempts have been made to reverse the clinical manifestations of experimentally-induced Parkinsonism by transplanting dopaminergic cells into the striatum of affected animals. Genetically modified fibroblasts (transfected with DNA encoding tyrosine hydroxylase) have been successfully transplanted into animals having lesions of dopaminergic pathways. Motor function and behavior of the animals improved following implantation of the dopamine producing fibroblasts. Wolff et al., *Proc. Natl. Acad. Sci. USA*, 86:9011–9014 (1989); Fisher et al., *Neuron*, 6:371–380 (1991). Graft survival may be enhanced, and hence clinical improvement prolonged, by transplantation of fetal tissue, as compared to cells obtained following birth. Gage and Fisher, *Neuron*, 6:1–12 (1991). Fresh fetal dopaminergic neurons have been transplanted into the caudate nucleus of monkeys following chemical injury to the nigrostriatal dopamine system. Following transplantation, the injury-induced behavioral deficits improved. Bankiewicz et al., *J. Neurosurg.*, 72:231–244 (1990) and Taylor et al., *Prog. Brain Res.*, 82:543–559 (1990).

Humans suffering from Parkinsonism have been treated by striatal implantation of dopaminergic neurons. Lindvall et al., *Arch. Neurol.*, 46:615–631 (1989); Widner et al., *New Engl. J. Med.*, 327:1556–1563 (1992). The transplanted cells were obtained from abortions. Prior to the abortions, the women were screened for antibodies to several disease causing viruses. Following surgery, the treated patients exhibited improvement of neurological function. The patients required maintenance immunosuppressive therapy, however.

Recent investigations indicate that trophic factors released from support cells of the central nervous system (e.g., astrocytes and oligodendrocytes) are critical to survival of neurons in cell culture. O'Malley et al., *Exp. Neurol.*, 112:40–48 (1991). Implanted fibroblasts that were genetically altered to express nerve growth factor have been shown to enhance survival of cholinergic neurons of the basal forebrain following injury to the fimbria-fornix which causes demise of acetylcholine neurons in the basal forebrain as seen in Alzheimer's disease. Rosenberg et al., *Science*, 242:1575–1577 (1988).

While previous attempts at cell transplant therapy for neurological disorders have provided encouraging results, several significant problems remain. The supply of fetal tissue for cellular transplants is quite limited. To ensure maximum viability, the fetal cells must be freshly harvested prior to transplantation. This requires coordinating the implantation procedure with elective abortions. Even then, fetal tissue has not been widely available in the United States. Also, the gestational age of the fetus from which cells are obtained influences graft survival. Gage and Fisher, supra. Obtaining fetal tissue of only certain gestational ages adds additional limitations to the availability of fetal cells for transplant. Further, ethical considerations make some potential transplant recipients reluctant to undergo the procedure when fresh fetal cells are implanted.

Because the fetal tissue is obtained from fresh abortuses, a significant risk of infectious contamination exists. Although women undergoing abortions which will supply fetal tissue are screened for a variety of infections, some infections, e.g., HIV, may not be clinically detectable and thus, not identified during the screening process. Therefore, if widely practiced, transplants of fresh fetal cells would likely cause many infectious sequelae.

Use of immortalized cell lines could overcome many of these difficulties of availability and infection. An immortalized human fetal neuro-derived cell line has been reported in Major et al., *Proc. Natl. Acad. Sci. USA*, 82:1257–1262 (1985) and U.S. Pat. No. 4,707,448. Further, immortalized cell lines, by their very nature, are predisposed to causing tumor formation following in vivo transplantation. Therefore, therapeutic intracerebral transplantations of immortalized cells carry a high risk of causing intracranial tumors, and even tumors having a benign histology may carry a poor prognosis when present within the calvarium.

In addition to the risk of tumor formation, transplants of genetically unrelated cells also carry the risk of immunological graft rejection and intracerebral inflammation. Widner and Brundin, *Brain Res. Rev.*, 13:287–324 (1988). All transplants of genetically unrelated cells carry this risk. Therefore, patients treated by intracerebral cell transplant have required long-term maintenance immunosuppression which, even in the absence of transplanted immortalized cells, carries a high risk of infectious and malignant complications. The transplantation of immortalized cells only magnifies the risk of these complications.

What is urgently needed in the art are methods of therapeutically implanting immortalized human fetal neuro-derived cells, and cell lines suitable for this use. Ideally, the methods would not result in tumor formation or elicit intense inflammation following transplantation. Desirably, the methods could employ cells derived from cell lines so that the risk of infectious contamination and limited cellular availability would be minimized. Quite surprisingly, the present invention fulfills these and other related needs.

SUMMARY OF THE INVENTION

The present invention provides methods for treating a host comprising implanting cells of an immortalized human neuro-derived fetal cell line into the host. Generally the cell line will be derived from human fetal astrocytes, such as the SVG cell line. The cells will often be implanted into the central nervous system of the host. The cells may be encapsulated by membranes which are impermeable to antibodies of the host.

In some embodiments of the invention, the cells may be transfected with a nucleic acid sequence encoding a peptide. The peptides will generally be enzymes, such as tyrosine hydroxylase, or growth factors, such as nerve growth factor. The peptide may also be a disease associated antigen. The cells may be implanted for purposes of treatment or prophylaxis. In some instances, the cells may be removed following implantation.

In additional embodiments, the present invention provides an immortalized human fetal neuro-derived cell line, which comprises a heterologous nucleic acid sequence, wherein the cell line is capable of expressing the heterologous nucleic acid sequence. Particularly preferred cell lines are capable of expressing a nucleic acid that encodes tyrosine hydroxylase. In more preferred aspects, the cell lines of the present invention are capable of expressing serotonin.

In a related embodiment, the present invention provides a transplantable composition which comprises the cell lines of the invention with a pharmaceutically acceptable carrier.

BRIEF DESCRIPTION OF THE DRAWINGS

Some of the figures include color photographs.

FIG. 1 demonstrates the morphology of SVG cells in vitro.

FIG. 2 illustrates immunoperoxidase staining of an antibody to SV40 T protein in SVG cells.

FIG. 17 shows a graph of the distribution of TH positive cell counts for dopaminergic cells plated at 100,000 cells per transwell chamber with and without SVG coculture. Shown is the number of TH positive rat mesencephalic cells remaining per transwell chamber (Y axis), when those cells were cultivated for 96 hours in the absence and presence of SVG cells. Coculture with SVG-TH cells produced identical results.

DESCRIPTION OF THE SPECIFIC EMBODIMENTS

Figure 3:
FIG. 3 demonstrates the needle track in the basal ganglia at low magnification.

The present invention generally relates to immortalized human fetal cell-lines derived from cells of the central nervous system, and methods of using these cell lines in treatment of disorders of the central nervous system. In particular, the cell lines and methods of the present invention may be used in the treatment of disorders caused by lesions in the central nervous system, such as Parkinsonism.

I. Methods of Treatment

In one embodiment, the present invention provides methods of treating a host suffering from a central nervous system disorder, or alleviating the symptoms of such a disorder, by implanting immortalized human fetal cells derived from cells of the central nervous system. Graft rejection, intense intracerebral inflammation, and tumor formation have not been demonstrated following implantation of such cells into the central nervous system. Further, the cells have been shown to induce neuron migration and neurite extension. This demonstrates that the cells are functioning to produce trophic factors that stimulate neuronal responses.

Implantation of immortalized human fetal cells derived from cells of the central nervous system provides a means of treating many diseases. For example, Parkinson's disease may be treated by implantation of these cells into the basal ganglia of an affected host. The trophic factors produced by the implanted cells may inhibit dopaminergic neuron demise and even induce dopaminergic neuron regeneration. The increased population of dopaminergic neurons can provide clinical improvement of persons suffering from Parkinsonism.

In additional embodiments, the implanted cells may be transfected with a nucleic acid which encodes a neurologically relevant polypeptide. The term "neurologically relevant peptide" generally refers to a peptide or protein which catalyzes a reaction within the tissues of the central nervous system. Such peptides may be naturally occurring neural peptides, proteins or enzymes, or may be peptide or protein fragments which have therapeutic activity within the central nervous system. Examples include neural growth factors, and enzymes used to catalyze the production of important neuro-chemicals, or their intermediates. In particularly preferred aspects, the cells will be transfected with a nucleic acid which encodes tyrosine hydroxylase. Tyrosine hydroxylase is the enzyme which converts tyrosine to L-DOPA, which is also the rate limiting step in the production of dopamine. Therefore, expression of tyrosine hydroxylase by the implanted cells allows these cells to produce and secrete dopamine. Thus, in addition to promoting neuronal regeneration, the implanted cells may increase the dopamine concentration in the substantia nigra and limit or reverse the effect of dopaminergic neuron loss.

The methods of the present invention may also be used to treat other neurological disorders such as Huntington's chorea, Alzheimer's disease, or multiple sclerosis. As immortalized human fetal neuro-derived cells are compatible with the central nervous system (CNS), these cells can also be transfected with DNA sequences encoding physiologically active peptides and implanted in the CNS, to effect treatment of other disorders. For instance, in Huntington's chorea and amyotrophic lateral sclerosis the peptide may block excitatory neurotransmitters such as glutamate. When applied to the treatment of multiple sclerosis, for example, the peptide would typically be a trophic stimulator of myelination, such as platelet derived growth factor or a ciliary trophic factor which may block oligodendrocyte demise. As these diseases are more generalized than local lesions, alternative implantation methods may be desirable. For example, the cells may be implanted on a surface exposed to cerebrospinal fluid. Following expression and secretion, the peptide will be washed over the entire surface of the brain by the natural circulation of the cerebrospinal fluid. Suitable sites for implantation include the lateral ventricles, lumbar thecal region, and the like. In Alzheimer's disease, the cells may be transfected to produce nerve growth factor to support neurons of the basal forebrain as described by Rosenberg et al., *Science*, 242:1575–1578 (1988), incorporated herein by reference.

The methods of the present invention may also be employed to treat hosts by implantation of cells in extra-neural sites. This embodiment of the present invention is particularly useful for prophylactic treatment of a host. Immortalized human fetal neuro-derived cells may be transfected with DNA encoding a disease-associated antigen, e.g., HIV gp120 polypeptides which encompass the principal neutralizing domain of HIV as described, e.g., in U.S. Pat. No. 5,166,050. The cells may then express and secrete the antigen encoded by the transfected DNA. The antigen may be continuously secreted by the implanted cells and elicit a strong immune response. Following an adequate time interval to fully immunize the host, the cells may be removed.

As used herein, "treating a host" includes prophylactic, palliative, and curative intervention in a disease process. Thus, the term "treatment" as used herein, typically refers to therapeutic methods for reducing or eliminating the symptoms of the particular disorder for which treatment is sought. The term "host," as used herein, generally refers to any warm blooded mammal, such as humans, non-human primates, rodents, and the like, which is to be the recipient of the particular treatment. Typically, the terms "host" and "patient" are used interchangeably herein to refer to a human subject.

A wide variety of diseases and syndromes may be treated by the methods of the present invention. Generally, the disease will be a neurological disease, such as Parkinsonism (including Parkinson's disease), Alzheimer's disease, Huntington's chorea, multiple sclerosis, amyotrophic lateral sclerosis, Gaucher's disease, Tay-Sachs disease, neuropathies, brain tumors, and the like. The methods of the present invention may also be employed in the treatment of non-neurological diseases. For example, the methods of the present invention may be used to immunize hosts against infectious diseases, such as viruses, bacteria, protozoa, and the like as described above. Immortalized human fetal neuro-derived cells may be transfected by DNA encoding physiologically active peptides or peptides which contain immunological epitopes. The methods of the present invention may be employed to implant the peptide producing cells and provide continuous in vivo delivery of other types of peptides, such as growth hormone, to the host.

II. Cell Lines

A. Generally

In order to practice the above described methods of treatment, the present invention also provides cell lines suitable for transplantation into a host or patient.

In general, the cells implanted by the methods of the present invention are immortalized human fetal neuro-derived cells. By "neuro-derived", it is meant that prior to immortalization, the cells had a neurological cell phenotype or were an embryonic cell committed to differentiation to a neurological cell type. Neurological cell types include neurons, astrocytes, oligodendrocytes, choroid plexus epithelial cells, and the like.

Preparation of the immortalized fetal cell lines may generally be carried out according to the following procedures. Fetal cells may be collected following elective abortion. Women donating fetuses following abortion will typically be serologically screened for a variety of infectious diseases, including human immunodeficiency virus, hepatitis B virus, hepatitis C virus, cytomegalovirus, and herpes viruses Types 1 and 2. Fetuses will generally be 9–11 weeks of gestational age (7–9 weeks postconception). Fetal age may be confirmed by ultrasound. Fetuses may be extracted under ultrasound guidance to minimize fetal brain trauma.

Following extraction, the fetal brain is identified and dissected from the abortus. The cells may be prepared as follows. Brain tissue is aspirated through a 19 gauge needle and washed twice in Eagle's minimum essential media (E-MEM, Gibco, New York, N.Y.). Cells are plated on culture dishes treated with poly-D-lysine (0.1 mg/ml for 5 minutes). The cells are grown on E-MEM supplemented with 20% fetal bovine serum, 75 µg/ml streptomycin, 75 units/ml penicillin, 1% dextrose and 2 µg/ml fungizone (Gibco). Prior to immortalization the cells are incubated at 37° C. in a 5% $CO_2$ humidified environment. One of skill in the art will recognize that other methods for preparing cells may also be used.

The cells to be implanted by the methods of the present invention can be immortalized by a variety of techniques. Typically, the cells will be immortalized as follows. The cell cultures will generally produce progenitor neuronal and glial cells, as well as neurons, as described by Major and Vacante, *J. Neuropath. and Exp. Neurol.*, 48:425–436 (1989), incorporated herein by reference. With regular refeeding, the brain cells will survive for several months but show little cell proliferation. Cells are transformed by transfection with a SV40 deletion mutant. The mutant DNA lacks an origin of replication (ori-) and can not multiply. Transfection of the DNA, however, will transform cells to unlimited growth potential as described by Gluzman, *Cell*, 23:175–182 (1981). After growing the fetal cell cultures for 3 weeks, the cells may be transfected with 100 µg/flask of plasmid DNA (pMK16) containing the SV40 ori- mutant using the calcium phosphate precipitation technique as described by Graham et al. *Virol.*, 52:456–467 (1973). Alternatively, the cells may be transfected by electroporation, or other well known techniques as described in Sambrook et al., *Molecular Cloning, A Laboratory Manual*, Cold Spring Harbor Press, 1988, incorporated herein by reference. Following transfection, the cultures are grown with weekly refeeding. After several weeks, proliferation of glial cells in separate areas of the plates becomes evident. The cells are then transferred by trypsinization (0.025%) to new cultures. Transformed cells may be identified by fluorescence antibody assays to detect the SV40 T protein which is expressed by transformed cells (FIG. 2). The cells are passaged every 10 days until an increase in the number of T protein positive cells is detected.

The transformed cells will display the phenotype of a continuous cell line. Specifically, the cells will grow to a high saturation density with an 18 hour generation time. The cells do not show the transformed phenotype or anchorage independent growth, however, which is characteristic of non-mutant SV40 transformed cells. The cell morphology is also not altered during the course of establishment of the cell line. Foci of cells are generally not detected. Particularly useful cells include those from the SVG cell line deposited with the American Type Culture Collection, Rockville Md., (A.T.C.C. CRL 8621) which is described in U.S. Pat. No. 4,707,448, incorporated herein by reference (FIG. 1). Hereinafter by "SVG cells" or "SVG cell line", it is meant cells or a cell line derived from cell line A.T.C.C. CRL 8621. By derivatives is meant a subclone, replication, or genetically altered mutant of cell line A.T.C.C. CRL 8621.

Alternatively, the cells may be immortalized by other techniques which are well known in the art. For example, immortalization by Epstein-Barr virus may be employed, as described in U.S. Pat. No. 4,464,465, incorporated herein by reference. Epstein-Barr virus mutants which lack OriP and OriLyt origins of replication are particularly useful. Another useful method of immortalization is over-expression of a cellular gene for growth control such as c-myc as described by Bartlett et al., *Proc. Natl. Acad. Sci. USA*, 85:3255–3259 (1988), incorporated herein by reference. Generally, transformed cells suitable for implantation will be anchorage dependent, will not grow in soft agar, and will not exhibit foci formation.

The histological origin of the transformed cells may then be determined. Characteristically, astroglial cells can be recognized by the presence of an intermediate filament composed of glial fibrillary acidic protein, GFAP. Oligodendroglial cells, on the other hand, are myelin producing cells and can be identified by their synthesis of a galactocerebroside, gal C, which is a component of myelin.

Following transformation, the cells will be prepared for implantation. The cells are suspended in a physiologically compatible carrier, such as cell culture medium (e.g., Eagle's minimal essential media) or phosphate buffered saline. Cell density is generally about $10^4$ to $10^7$ cells/ml. The cell suspension is gently rocked prior to implantation. The volume of cell suspension to be implanted will vary depending on the site of implantation, treatment goal, and cell density in the solution. Typically, the amount of cells transplanted into the patient or host will be a "therapeutically effective amount." As used herein, a therapeutically effective amount refers to the number of transplanted cells which are required to effect treatment of the particular disorder for which treatment is sought. For example, where the treatment is for Parkinsonism, transplantation of a therapeutically effective amount of cells will typically produce a reduction in the amount and/or severity of the symptoms associated with that disorder, e.g., rigidity, akinesia and gait disorder. In the treatment of Parkinsonism, 5 µl to 60 µl of cell suspension will typically be administered in each injection to achieve this effective amount. Several injections may be used in each host. Persons of skill will understand how to determine proper cell dosages.

In alternative preferred embodiments of the present invention, the cells which are useful for transplantation, may be transfected with, and capable of expressing, a heterologous nucleic acid sequence which encodes a neurologically relevant peptide. The term "heterologous" as used to describe the nucleic acids herein, generally refers to a sequence which, as a whole, is not naturally occurring within the cell line transfected with that sequence. Thus, the heterologous sequence may comprise a segment which is entirely foreign to the cell line, or alternatively, may comprise a native segment which is incorporated within the cell line in a non-native fashion, e.g., linked to a non-native promoter/enhancer sequence, linked to a native promoter which is not typically associated with the segment, or provided in multiple copies where the cell line normally provides one or no copies.

Generally, the nucleic acid sequence will be operably linked to a transcriptional promoter and a transcriptional terminator. A DNA segment is operably linked when it is placed into a functional relationship with another DNA segment. For example, a promoter or enhancer is operably linked to a coding sequence if it stimulates the transcription of the sequence; DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The DNA sequence may also be linked to a transcriptional enhancer. Expression of the DNA in the implanted cells may be constitutive or inducible. A variety of expression vectors having these characteristics may carry the DNA for transfection of the cells, such as plasmid vectors pTK2, pHyg, and pRSVneo, simian virus 40 vectors, bovine papillomavirus vectors or Epstein-Barr virus vectors, as described in Sambrook et al., *Molecular Cloning, A Laboratory Manual*, Cold Spring Harbor Press, 1988, previously incorporated herein by reference. The vectors may be introduced into the cells by standard methods, such as electroporation, calcium phosphate-mediated transfection, polybrene transfection, and the like.

The peptide encoded by the nucleic acid may generally be a directly therapeutic compound, such as a movement inhibitor in the treatment of Huntington's chorea. Alternatively, the peptide encoded by the nucleic acid may be selected to supplement or replace deficient production of the peptide by the endogenous tissues of the host, which deficiency is a cause of the symptoms of a particular disorder. In this case, the cell lines act as an artificial source of the peptide. Alternatively, the peptide may be an enzyme which catalyzes the production of a therapeutic, or neurologically relevant compounds. Again, such compounds may be exogenous to the host's system, or may be an endogenous compound whose synthesis pathway is otherwise impaired. In this latter case, production of the peptide within the CNS of the host provides supplemental pathways for the production of the compound. For example, in a preferred embodiment, the immortalized human fetal neuro-derived cell lines are transfected with a nucleic acid which encodes a tyrosine hydroxylase enzyme. Tyrosine hydroxylase catalyzes the synthesis of L-dopa from tyrosine. Dopamine has been demonstrated to be effective in the treatment of Parkinsonism.

In particularly preferred aspects, the immortalized neuro-derived fetal cell lines which are transfected with a tyrosine hydroxylase encoding nucleic acid will be an SVG cell line, e.g., those from the SVG cell line deposited with the American Type Culture Collection, Rockville MD, (A.T.C.C. CRL 8621) which is described in U.S. Pat. No. 4,707,448, incorporated herein by reference (FIG. 1). Such cell lines are referred to herein as SVG-TH cell lines. In still more preferred aspects, the SVG cell line is transfected with a phTH/Neo plasmid.

The nucleic acid may also encode a trophic factor such as a nerve growth factor, an inhibitory growth factor, or a cytokine useful in the treatment of brain tumors.

Due to their ability to enhance neural regeneration and produce and secrete L-dopa, the cell lines of the present invention are particularly useful in the treatment of central nervous system disorders which are associated with the loss of dopaminergic cells in the CNS of the host, such as Parkinsonism. Surprisingly, it has also been discovered that the cell lines of the present invention are also capable of producing additional neurotransmitters. In a particularly preferred embodiment, for example, the cell lines of the present invention are also capable of expressing serotonin. Serotonin has been implicated in occurrences of clinical depression in human subjects. Specifically, increasing serotonin levels in the tissues of the central nervous system have been found to alleviate symptoms of depression, and form the basis of a number of antidepressant treatments, e.g Prozac™. As such, the cell lines of the present invention may also be particularly useful in methods for the treatment of disorders associated with reduced serotonin levels in the CNS, such as depression. Typically, these methods are the same or substantially similar to the methods described herein for the treatment of other disorders of the nervous system.

For sufferers of Parkinsonism, the cell lines of the present invention therefore have a two-fold benefit of alleviating the symptoms of the disorder through the secretion of L-dopa and neural regeneration, as well as treating the depression associated with the disorder through the secretion of serotonin.

III. Implantation of Cell Lines

Typically, the cells from the cell lines of the present invention may be implanted within the parenchyma of the brain, in a space containing cerebrospinal fluid, such as the sub-arachnoid space or ventricles, or extraneurally. As used herein, the term "extraneurally" is intended to indicate regions of the host which are not within the central nervous system or peripheral nervous tissue, such as the celiac ganglion or sciatic nerve. "Extraneural" regions may contain peripheral nerves. "Central nervous system" is meant to include all structures within the dura mater.

When the cells are implanted into the brain, stereotaxic methods will generally be used as described in Leksell and Jernberg, *Acta Neurochir.*, 52:1–7 (1980) and Leksell et al., *J. Neurosurg.*, 66:626–629 (1987), both of which are incorporated herein by reference. Localization of target regions will generally include pre-implantation MRI as described in Leksell et al., *J. Neurol. Neurosurg. Psychiatry*, 48:14–18 (1985), incorporated herein by reference. Target coordinates will be determined from the pre-implantation MRI.

Prior to implantation, the viability of the cells may be assessed as described by Brundin et al., *Brain Res.*, 331:251–259 (1985), incorporated herein by reference. Briefly, sample aliquots of the cell suspension (1–4 µl) are mixed on a glass slide with 10 µl of a mixture of acridine orange and ethidium bromide (3.4 µg/ml of each component in 0.9% saline; Sigma). The suspension is transferred to a hemocytometer, and viable and non-viable cells were visually counted using a fluorescence microscope under epi-illumination at 390 nm, combined with white light trans-illumination to visualize the counting chamber grid. Acridine orange stains live nuclei green, whereas ethidium bromide will enter dead cells resulting in orange-red fluorescence. Cell suspensions should generally contain more than about 98% viable cells.

Injections will generally be made with sterilized 10 µl Hamilton syringes having 23–27 gauge needles. The syringe, loaded with cells, are mounted directly into the head of a stereotaxic frame. The injection needle is lowered to predetermined coordinates through small burr holes in the cranium. 40–50 µl of suspension are deposited at the rate of about 1–2 µl/min. and a further 2–5 min. are allowed for diffusion prior to slow retraction of the needle. Frequently, two separate deposits will be made, separated by 1–3 mm, along the same needle penetration, and up to 5 deposits scattered over the target area can readily be made in the same operation. The injection may be performed manually or by an infusion pump. At the completion of surgery following retraction of the needle, the host is removed from the frame and the wound is sutured. Prophylactic antibiotics or immunosuppressive therapy may be administered as needed.

For treatment of more generalized neurological disorders, cells may be transfected to express a therapeutic compound and implanted in the ventricles or lumbar theca. As the therapeutic compound is secreted by the cells, natural circulation of the cerebrospinal fluid washes the therapeutic compound throughout the central nervous system providing a means of generalized treatment. Implantation into the ventricles may be accomplished by an open procedure, such as described in Madrazo et al., *New Engl. J. Med.*, 316:831–834 (1987) or Penn et al., *Neurosurgery*, 22:999–1004 (1988), both of which are incorporated herein by reference. Implantation of cells into the lumbar theca is most conveniently accomplished by standard procedures similar to instillation of radiographic contrast media or antitumor medication via a lumbar puncture.

In some instances, it may be desirable to implant cells extraneurally according to the present invention. The cells may be implanted percutaneously through a needle or endoscope or by an open procedure. Persons of skill will readily appreciate the most appropriate method of implanting cells for particular applications.

The cells may be encapsulated by membranes prior to implantation. The encapsulation provides a barrier to the host's immune system and inhibits graft rejection and inflammation. Several methods of cell encapsulation may be employed. In some instances, cells will be individually encapsulated. In other instances, many cells will be encapsulated within the same membrane. When the cells will be removed following implantation, the relatively large size of a structure encapsulating many cells within a single membrane provides a convenient means for retrieval of the implanted cells. Several methods of cell encapsulation are well known in the art, such as described in European Patent Publication No. 301,777, or U.S. Pat. Nos. 4,353,888, 4,744, 933, 4,749,620, 4,814,274, 5,084,350, or 5,089,272, each of which is incorporated herein by reference.

One method of cell encapsulation is as follows. The transformed cells are mixed with sodium alginate (a polyanionic seaweed extract) and extruded into a solution of divalent cations, e.g., calcium chloride, which complexes with the sodium alginate to form a gel, resulting in the formation of gelled beads or droplets which contain the cells. The gel beads are incubated with a high molecular weight (MW 60–500×$10^3$) concentration (0.03–0.1% w/v) polyamino acid, such as poly-L-lysine, for a brief period of time (3–20 minutes) to form a membrane. The interior of the formed capsule is reliquified by treating with sodium citrate. The single membrane around the cells is highly permeable (MW cut-off 200–400×$10^3$). The single membrane capsule containing the cell is incubated in a saline solution for 1–3 hours to allow entrapped sodium alginate to diffuse out of the capsule and expand the capsule to an equilibrium state. The resulting alginate-poor capsule is reacted with a low molecular weight polyamino acid (MW 10–30×$10^3$) such a poly-L-lysine (PLL) or chitosan (deacetylated chitin; MW 240×$10^3$) to produce an interacted, less permeable membrane (MW cut-off 40–80×$10^3$). The dual membrane encapsulated cells are then cultured in E-MEM for two to three weeks as described above.

While reference has been made specifically to sodium alginate beads, it will be appreciated by those skilled in the art that any non-toxic water soluble substance that can be gelled to form a shape-retaining mass by a change in conditions in the medium in which it is placed may be employed. Such gelling material generally comprises several chemical moieties which are readily ionized to form anionic or cationic groups so that the surface layers can cross link to form a permanent membrane when exposed to oppositely charged polymers. Most polysaccharide gums, both natural and synthetic, can be cross-linked by polymers containing positively charged reactive groups such as amino groups. The cross-linking biocompatible polymers which may be reacted with the sodium alginate gum include polylysine and other polyamino acids. The degree of permeability of the membrane formed may be controlled by careful selection of a polyamino acid having the desired molecular weight. Poly-L-lysine (PLL) is the preferred polymeric material but others include chitosan and polyacrylate. Molecular weights typically vary from about $10^4$ to about $10^6$.

The present invention is further illustrated by the following examples. These examples are merely to illustrate aspects of the present invention and are not intended as limitations of this invention.

EXAMPLE 1

Preparation of SVG Cells

This example describes preparation of SVG cells (A.T.C.C. CRL 8621) for implantation into rhesus monkeys. The cells were screened for infection with mycoplasma, HIV-1, Hepatitis B virus, virus, simian virus 40, Herpes simplex virus, cytomegalovirus, and JC virus.

SVG cells were grown to confluency. Cell growth was anchorage dependent. Foci formation did not occur and cell morphology was homogeneous. The cells were removed from tissue culture plates by digestion with 0.05% trypsin in 0.1M EDTA (Versene Buffer) in Hank's balanced salt solution. Cells were collected by centrifugation, washed 3 times and resuspended in phosphate buffered saline. Final cell density was $10^6$ cells/ml. The cell suspension was stored at 4° C. until transplantation.

EXAMPLE 2

Implantation of SVG Cells

This example describes implantation of SVG cells into the basal ganglia of six rhesus monkeys. The implantations were performed by stereotaxic methods without surgical complications.

The animals were initially anesthetized with ketamine and were maintained on isofluorine gas anesthesia during the course of the surgery. Animals were placed in the stereotaxic frame (Kopf) and the landmarks for implantation were established through the stereotactic coordinates. The superior sagittal sinus was exposed in order to establish the midline. Marks were placed on the cranium over the caudate and the putamen on both sides. The coordinates were as follows: AP was +24 mm in front of the 0. Lateral coordinates were 5 mm from the midline for the caudate nucleus, and 10 mm lateral from the midline for the putamen.

Five burr holes were made. One was made over the superior sagittal sinus, two over the caudates and two over the putamens. Two different implantation techniques were used.

1. 10 μl Hamilton syringes with 26 gauge needle or 50 μl Hamilton syringes with 23 gauge needles were used. On the right side of the brain SVG cells were transplanted. Using the syringes, two deposits were done in the putamen. One deposit was in the lateral putamen and the second was in the medial putamen. The needles were lowered at 18 mm from the cortex, then 10 μl of the cell suspension was implanted using the Kopf microinjector. After the first implantation the needle was removed 1 mm a minute for 3 mm and then the second injection of 10 μl of the cell suspension followed.

After the second injection the needle was removed at 1 mm per minute. A second implantation was done in the opposite putamen at the same coordinates with the same technique.

After injecting the putamen, implantation into the caudate nucleus was performed with the same cell suspension. Two injections were done into the caudate, in the lateral and medial aspects. The depth of the injection was 15 mm and 10 μl was implanted. The syringe was withdrawn 1 mm per minute for 3 mm, then the second injection of 10 μl of the cell suspension was performed. Non-transfected SVG cells were transplanted into the putamen and SVG cells transfected with the tyrosine hydroxylase gene were transplanted into the caudate. The concentration of the cells was $2 \times 10^6$ cells per mL.

2. In addition to using implantation with the syringes with needles, cannulas of blue peek tubing connected to 22 gauge needles were constructed. The tubing was connected to 1 cc tuberculin syringes using 0 dead volume connectors. Following insertion into the target, the needle was allowed to stand for 15 minutes prior to infusion. A Harvard infusion pump holding the cell suspension was then started at 0.2 μl/min. After infusing for 15 minutes at 0.2 μl/min, the rate was increased to 0.4 μl/min and was continued for 100 minutes. After termination of the infusion, the needles were left in place for 30 minutes prior to withdrawal. The needles were then very slowly removed from the brain.

The wound was rinsed and then closed in anatomical layers. The animals woke up from the anesthesia and were transferred to their home cages 20 minutes after surgery.

EXAMPLE 3

Engrafting of SVG Cells into Monkeys

This example demonstrates successful engrafting of the implanted SVG cells in two of the monkeys sacrificed one month following implantation. The transplanted cells were histologically healthy. There was no evidence of inflammation or tumor formation.

The brain tissue in the region of the implantations was examined as follows:

For histopathological studies animals were killed by an overdose of pentobarbital (460 mg, i.v.) and were perfused through the ascending aorta with 15 ml of ice cold phosphate-buffered saline (PBS) followed by 10% formalin. The brains were removed rapidly, cut into 6 mm coronal slices and postfixed for 30 min. in the same fixative. The tissue slices were rinsed for 48 hr. in 30% sucrose in PBS and then rapidly frozen in −70° C. Tissue was cut into 40 μm coronal sections in a freezing microtome and series of sections were collected in PBS. Sections were processed for immunohistochemistry with antibodies against tyrosine hydroxylase, glial fibrillary acidic protein and T-protein. Sections adjacent to those examined for TH-IR were stained with hematoxylin and eosin. Some blocks of tissue containing implant were processed in 5 μm paraffin sections and were stained as described above.

Figure 4:
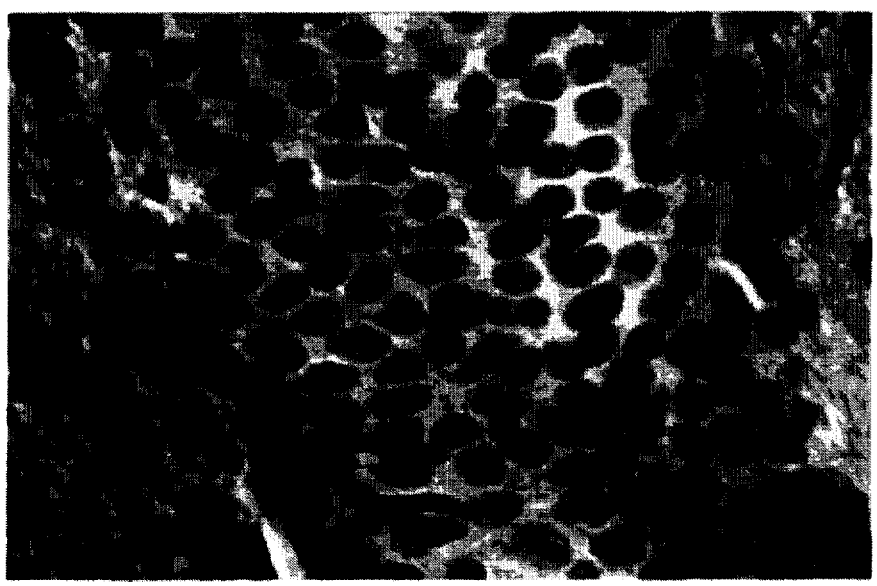
FIG. 4 illustrates a high magnification view of a needle track in the basal ganglia.
Figure 5:
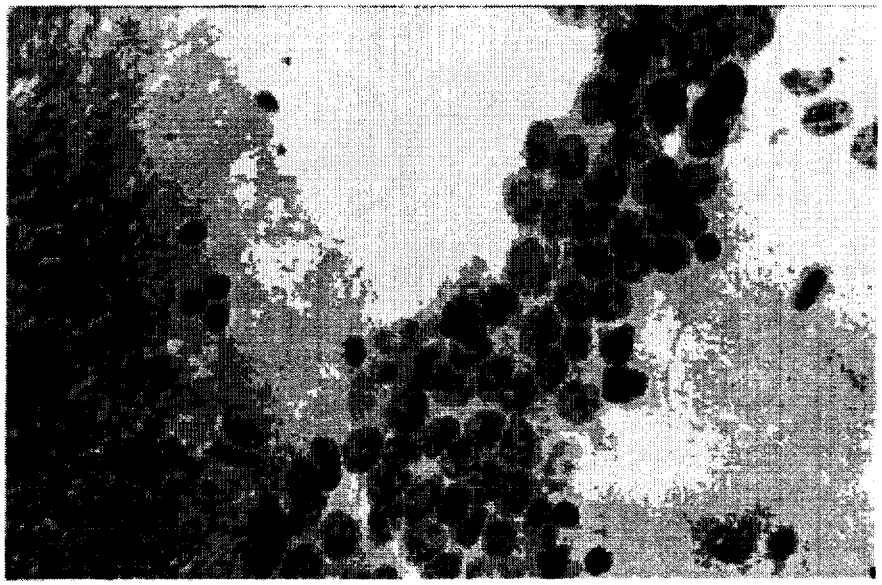
FIG. 5 demonstrates another high magnification view of a needle track in the basal ganglia.

FIG. 3 illustrates the needle track in a basal ganglia of one of the monkeys at low power. Higher power views of the needle track (FIGS. 4–5) demonstrate viable SVG cells in the track. The cells are readily identified by large nucleus containing multiple nucleoli as exhibited by SVG cells in vitro. The morphology of the implant cells is strikingly different than the morphology of surrounding cells. Inflammatory cells and tumor formation was not identified.

Identical tests were performed on monkeys sacrificed at nine months post transplantation. The graft was identified and no evidence of inflammatory cells or tumor formation was discovered, indicating that the cells had engrafted and had not been rejected by the host.

EXAMPLE 4

MRI Evaluation of Engrafted SVG Cells

This example describes cerebral MRI evaluation one month following implantation of the four remaining monkeys. No evidence of tumor formation was present in any of the monkeys.

Figure 9:
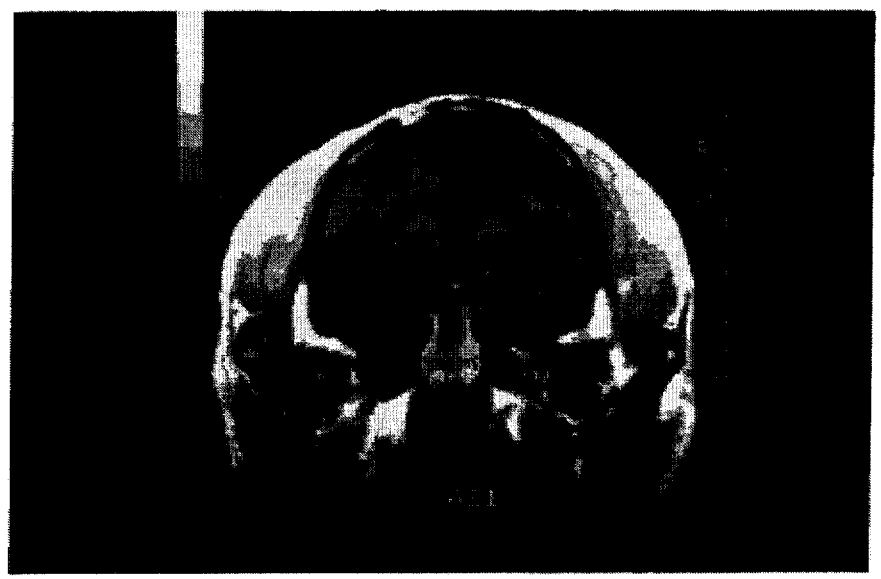
FIG. 9 demonstrates a $T_1$ weighted MRI (with gadolinium enhancement) of a monkey brain 6 months following implantation.

Following induction of anesthesia, the monkeys were placed in a standard MRI frame. $T_1$ and $T_2$ weighted images without contrast and $T_1$ weighted images with gadolinium were done using a 1.5 Tesla magnet (Signa). The scans revealed no evidence of tumor or nodule formation (FIG. 9).

EXAMPLE 5

This example demonstrates functioning of the transplanted SVG cells within the central nervous system. Host neurons migrated toward the implanted cells, neuronal dopaminergic bodies, and dopaminergic processes of host origin were extended to the implanted cells.

Two of the surviving monkeys which received SVG cell implants as described in Example 2 above were sacrificed as described. The brains were removed intact as described above and sectioned.

Figure 6:
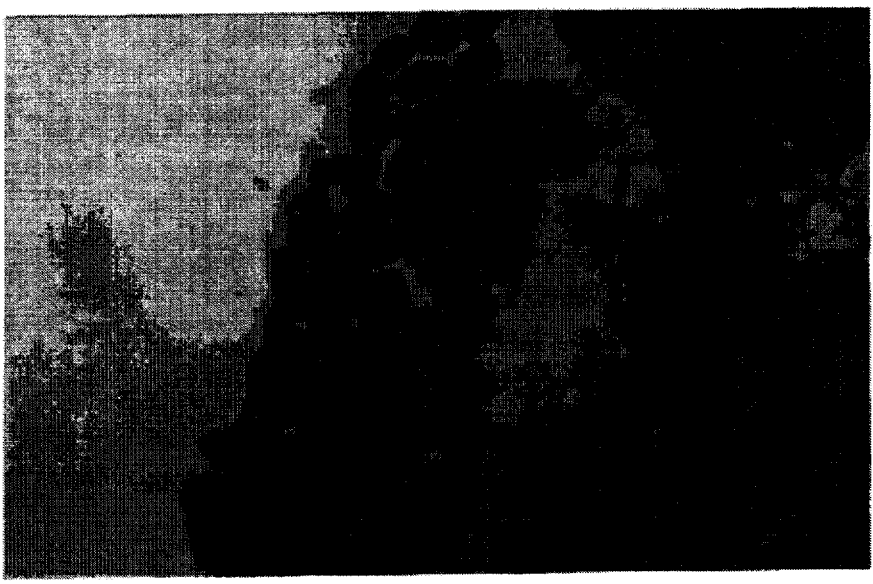
FIG. 6 demonstrates a nest of SVG cells on the wall of the lateral ventricle.
Figure 7:
FIG. 7 illustrates implanted SVG cells on the wall of the lateral ventricle stained with an antibody to glial fibrillary acidic protein.
Figure 8:
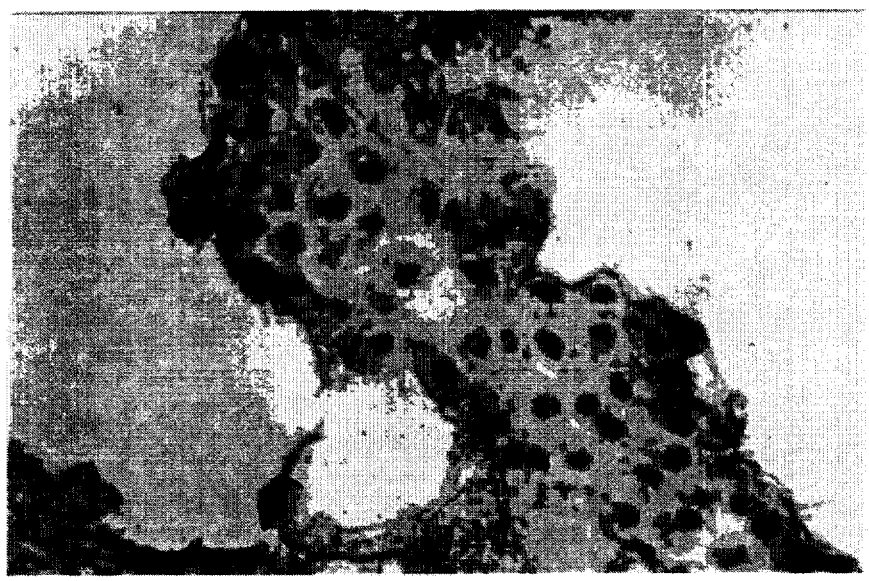
FIG. 8 demonstrates an in vivo section of implanted SVG cells stained with anti-T protein antibody.

Each section was placed on gelatin coated slides. Representative sections were stained with hematoxylin and eosin to characterize the anatomy (FIG. 6). The implanted cells exhibited characteristic SVG morphology with large nuclei having multiple nucleoli. Adjacent sections were stained with either monoclonal antibody to glial fibrillary acidic protein (GFAP), SV40 T protein, or tyrosine hydroxylase. The sections were then counterstained with hematoxylin alone. FIG. 7 illustrates an adjacent section stained with antibody to GFAP, a cytoplasmic protein of astrocytic lineage. The astrocytic origin is demonstrated by the dense cytoplasmic staining. The origin of the cells is also illustrated in FIG. 8 which clearly shows implanted cells stained with anti-T protein antibody.

Figure 10:
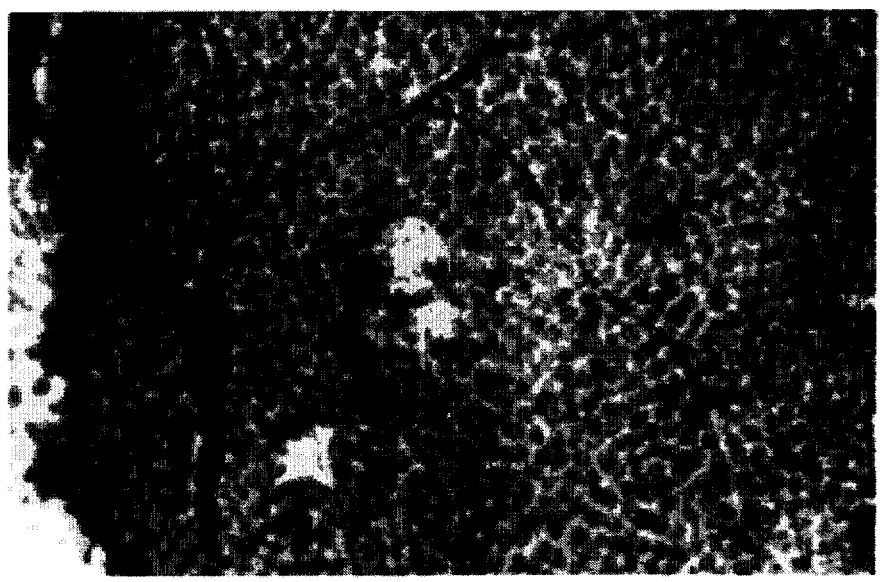
FIG. 10 demonstrates growth of a tyrosine hydroxylase neuron on a layer of implanted SVG cells in vivo.

The grafted cells within the caudate and putamen were viable and easily identified by anti-protein T antibody as described above. SVG cells were also identified on the wall of the lateral ventricles of all monkeys. Dopaminergic neurons exhibited neurite outgrowth toward the implanted cells (FIG. 10 demonstrates a tyrosine hydroxylase neuron stained with anti-tyrosine hydroxylase antibody in a layer of SVG cells in vivo). Dopaminergic neuronal bodies were also present in the region of the implanted SVG cells. The neurite outgrowth and presence of neuronal bodies indicate that the SVG cells produced neurotropic factors which caused neuron migration and extension of neuronal processes.

No evidence of inflammation, graft rejection, tumor or nodule formation was found in any of the sections.

EXAMPLE 6

Encapsulation of SVG Cells

This example describes individual encapsulation of SVG cells and preparation of the cells for implantation. The cells are encapsulated in a sodium alginate pellet.

SVG cells are grown to confluence in culture dishes. The cells are removed from the culture plates with 0.05% trypsin and 1 mM EDTA in Dulbecco's phosphate-buffered saline (PBS). The cells are suspended in PBS supplemented with $MgCl_2$, $CaCl_2$, 0.1% glucose, and 5% fetal bovine serum. Cells are collected by centrifugation, washed twice in the suspension solution as described above and centrifuged to a pellet.

The cell pellet remaining at the bottom of the centrifuge tube is resuspended in 5 ml of a 1.5% (w/v) sodium alginate solution (Keltone LV® by Kelco, Ltd., Chicago, Ill.). The alginate cell suspension is extruded into 50 ml of a 1.5% (w/v) $CaCl_2$ solution. Spherical droplets of the suspension are formed by an air jet-syringe pump droplet generator. With this apparatus, the cell-sodium-alginate suspension is extruded through a 22-gauge needle located inside a sheathed tube (3 mm I.D.) through which air flowed at a controlled rate (9 L min). As liquid droplets are forced out of the end of the needle by the syringe pump (at 20 cc hr), the droplets are pulled off by the shear forces set up by the rapidly flowing air stream. The needle tip is kept 8 cm above the surface of the $CaCl_2$ solution surface to ensure that uniform, spherical gel droplets are formed with a diameter of about 300–1000 microns.

A sample of the gelled microbeads is examined for size and shape consistency using a dissecting microscope (Wild Heerbrugg Model M8) fitted with a calibrated eye-piece. After transferring the calcium alginate gel beads, containing the immobilized cells, to a 50 ml plastic centrifuge tube with a conical bottom, the beads are washed with 30 ml each of 0.1% (w/v) CHES and 1.1% (w/v) $CaCl_2$ solutions. The supernatant volume is reduced after each washing using a vacuum aspirator. A semi-permeable capsule membrane is formed by reacting the gel droplets with an aqueous 0.05% (w/v) PLL solution (M/v of PLL=22.000) for 8 minutes. After the addition of the PLL solution, the centrifuge tube is capped and manually rocked end-to-end for the duration of the reaction to keep the capsules from sticking together. The resultant microcapsules, 300–1000 microns in diameter, are washed with 30 ml each of 0.1% CHES and 1.1% $CaCl_2$ and with two 30 ml aliquots of isotonic saline. The encapsulated cells are contacted with 30 ml of 0.03% (w/v) sodium alginate solution for 4 minutes formed an outer layer on the capsules. The interior of the microcapsules is liquified with 30 ml of a 0.05M sodium citrate solution for six minutes. The microcapsules, 400–1400 microns in diameter, are washed several times in saline to remove excess citrate and then divided into five 1 ml aliquots. Each aliquot is incubated in 10 ml DMEM medium in a 25 $cm^3$ culture flask at 37° C. in an isotemp Series 400 $CO^2$ incubator (model 413D, Fisher Scientific Co., Nepean, Ontario).

EXAMPLE 7

Genetic Engineering of SVG Cells to Express Tyrosine Hydroxylase

This example describes transfecting SVG cells with nucleic acid encoding tyrosine hydroxylase. SVG cells which expressed tyrosine hydroxylase were identified in the cultures following transfection.

Figure 11:
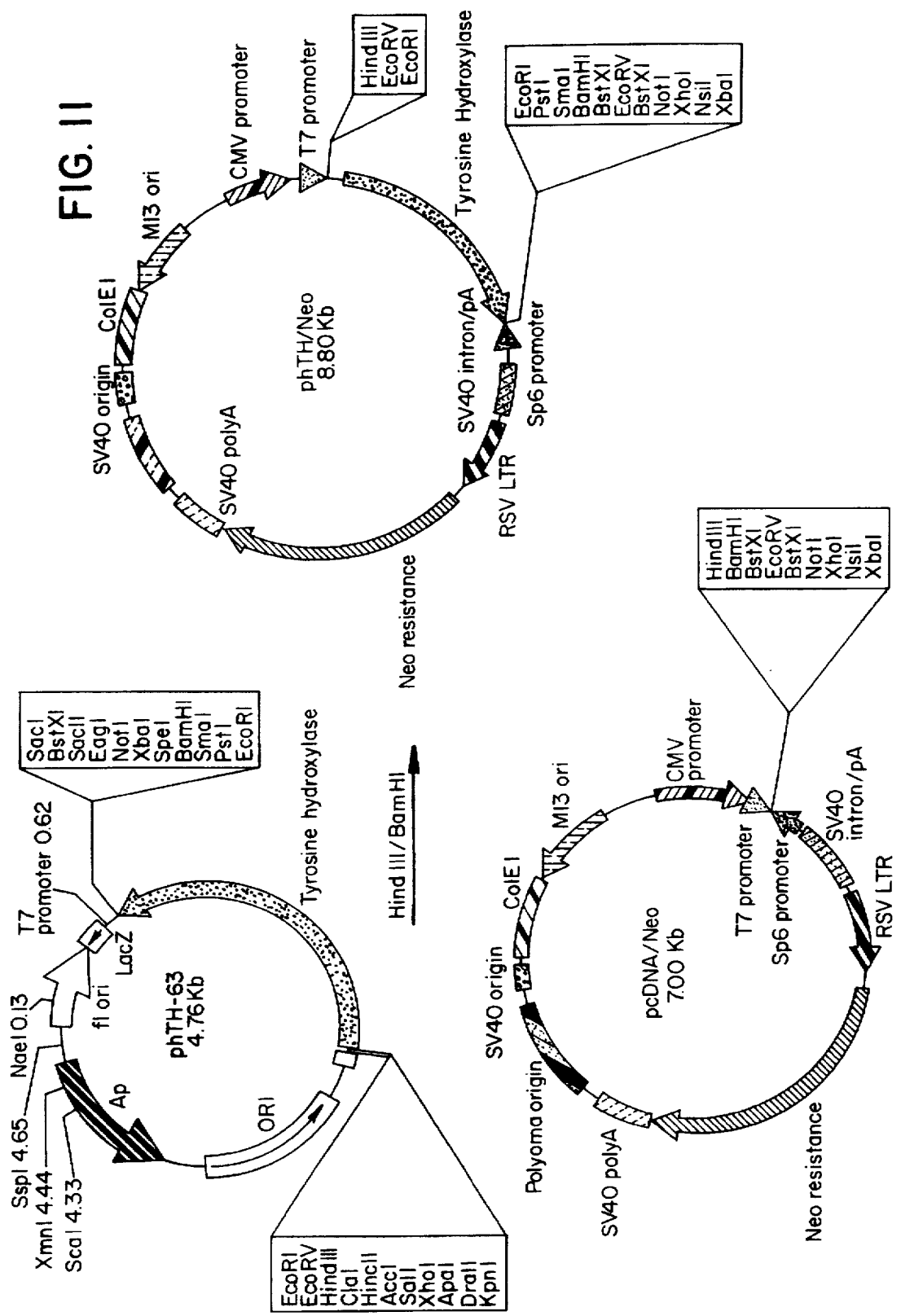
FIG. 11 shows a schematic representation of the construction of the phTH/Neo plasmid used in constructing the SVG-TH cell lines.

The SVG cell line was transfected with a nucleic acid which encodes the enzyme tyrosine hydroxylase (TH). Plasmid phTH-63 has the type 2 cDNA for tyrosine hydroxylase cloned into the EcoR1 site of Bluescript vector KS. The TH cDNA was cloned into two different eukaryotic expression vectors, pcDNA/Neo and pRSV/Neo (Both available from Invitrogen, Corp., San Diego, Calif.). A HindIII/BamH1 fragment of phTH-63 which contains the TH cDNA was cloned into the HindIII/Hind1 site of pcDNA/Neo, resulting in plasmid phTH/Neo. Similarly, a HindIII/Spe1 fragment of phTH-63 which contains the TH CDNA was cloned into the HindIII/Spe1 site of pRc/RSV, resulting in plasmid pRSV-hTH/Neo. As seen in FIG. 11, phTH/Neo consists of the immediate early CMV promoter upstream from the TH cDNA, on a plasmid which confers neomycin resistance. The pRSV-hTH/Neo construct consists of the RSV LTR upstream from the TH cDNA, on a plasmid which confers neomycin resistance.

Figure 12:
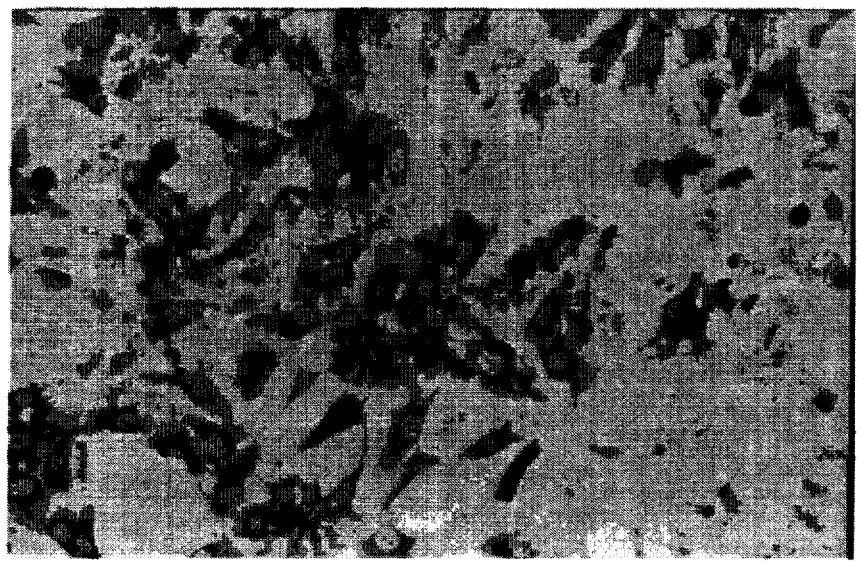
FIG. 12 shows tyrosine hydroxylase immunohistochemical staining of a stable phTH/Neo transfectant.
Figure 13:
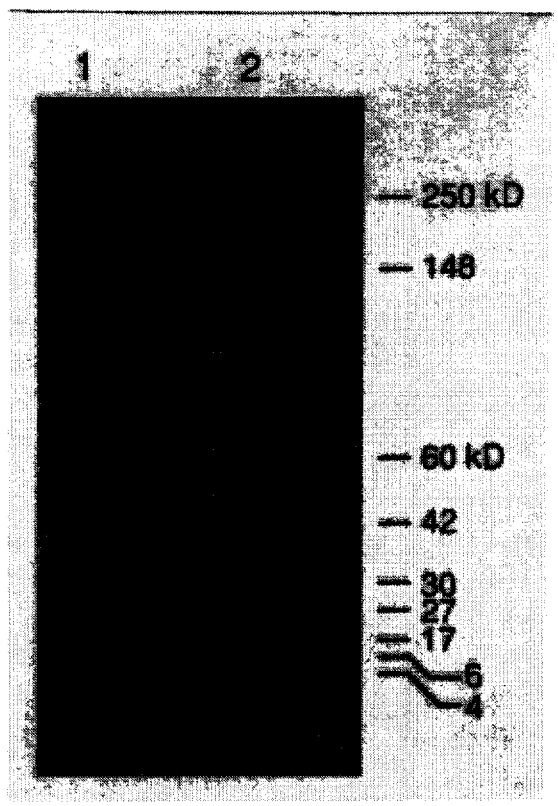
FIG. 13 shows western blotting of one TH positive clone (1B1B) which confirms the immunohistochemistry shown in FIG. 12.

Separate cultures of SVG cells were established and each was transfected with either phTH/Neo or pRSV-hTH/Neo. Following transfection, the cells were grown in media containing geneticin at 500 micrograms/ml for two months. Seven clones that were stably resistant to geneticin were established from the phTH/Neo transfection. Both transfectants were able to produce TH, however, no long-term stable clones were established using the pRSV-hTH/Neo construct, due to the weak expression of the neomycin resistance marker in this plasmid. Tyrosine hydroxylase immunohistochemical staining of one of the stable phTH/Neo transfectants is seen in FIG. 12. The clones ranged from 30% to 60% TH positive. One clone (1B1B) which was 40–60% TH positive was expanded and Western Blotting was done to confirm the immunohistochemistry. As seen in FIG. 13, when the Western blot was probed with a polyclonal antibody to TH, a band migrating at approximately 60 Kd was detected, consistent with the size of type 2 TH. The 1B1B clone was subsequently designated SVG-TH.

To determine whether there was biologically active TH in the SVG-TH cells and to determine whether there was secretion of L-dopa by the cells, HPLC analysis was performed on the cell culture supernatant. Cells were incubated with 1 mM biopterin ($BH_4$), a cofactor necessary for TH function, prior to collecting the cell culture supernatant for HPLC analysis. Controls included supernatant from SVG-TH cell cultures incubated in the absence of biopterin as well as supernatant from the cultures of the parental SVG cell line, incubated either with or without biopterin. The results are shown in Table 1, below.

TABLE 1

| L-Dopa Production in Supernatant of SVG and SVG-TH Cell Cultures Incubated With and Without $BH_4$ | | |
|---|---|---|
| L-Dopa | SVG Cells | SVG-TH Cells |
| Without $BH_4$ | Not Detectable | Not Detectable |
| With $BH_4$ (1 mM) | Not Detectable | 4–6 pmol/ml/min |

As shown in Table 1, L-dopa could not be detected from the parental SVG cell culture, either with or without biopterin, and could not be detected in the SVG-TH cell culture which was incubated without biopterin. However, when the SVG-TH cells were incubated with biopterin, approximately 4–6 pg/ml/min of L-dopa was produced in the cell culture supernatant. This confirmed that the TH seen on immunohistochemistry and Western blotting was biologically active.

Figure 14:
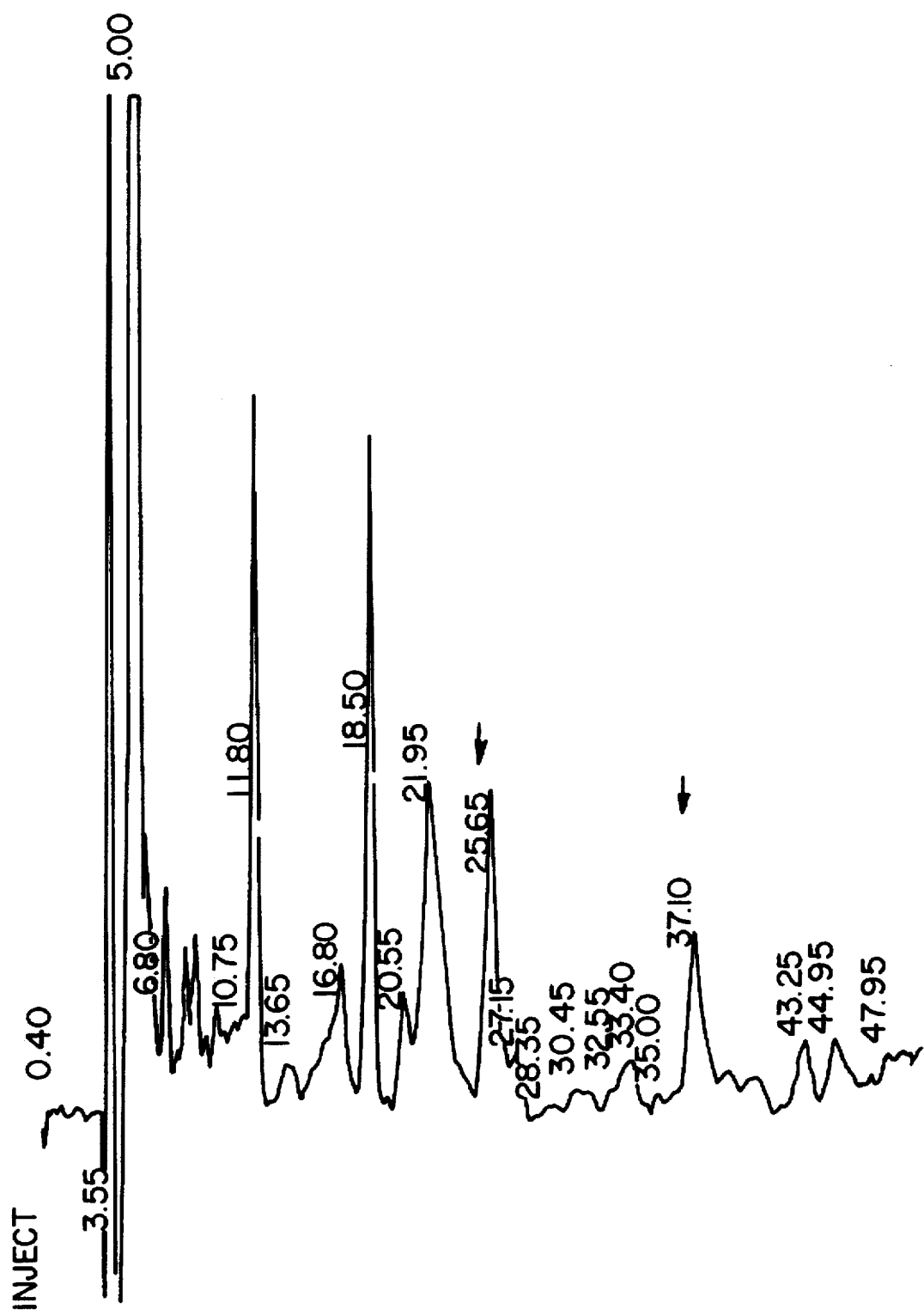
FIG. 14 shows a chromatogram from HPLC analysis of SVG-TH cell culture supernatant. Two peaks, at retention time of 25.65 and 37.1 minutes corresponded to retention times for serotonin and 5-hydroxyindolacetic acid, a main metabolite of serotonin, respectively. This was confirmed by immunohistochemical staining of SVG-TH cells for serotonin.

Unexpectedly, two other prominent peaks were also seen on the HPLC analysis of the supernatant from the SVG-TH cell culture (FIG. 14), independent of biopterin addition to the media. These two peaks were not seen in the parental SVG cell line. Using a series of standards, it was determined that the one of the two peaks represented serotonin and the second peak represented 5-hydroxyindoleacetic acid (5-HIAA), the breakdown product of serotonin. To confirm the presence of serotonin in these cells, immunohistochemistry of the SVG-TH cells was done using a polyclonal antibody to serotonin. The SVG-TH cells were positive for serotonin by immunostaining as well as by HPLC. The production of serotonin by these cell lines is unique for cells of glial origin, which have not been reported to produce serotonin.

The SVG-TH cells were characterized by immunohistochemical methods, using the same panel of antibodies as were used to characterize the SVG cells. The comparative results are shown in Table 2, below.

TABLE 2

|  | SVG | SVG-TH |
| --- | --- | --- |
| Vimentin | + | + |
| GFAP | weakly + | − |
| MHC Class I | + | + |
| MHC Class II | − | − |
| Thy 1.1 | + | + |
| T protein | + | + |
| Serotonin | − | + |
| l-dopa (HPLC) | − | + |
| NSE | − | − |
| Neurofilament | − | − |

Figure 15:
FIG. 15 shows an electron micrograph of SVG-TH cells.

An EM study of the SVG-TH cells revealed a marked dilatation of the rough ER not seen in the parental SVG cell line (FIG. 15). Coated pits, mitochondria and ribosomes were again easily identified.

EXAMPLE 8

Promotion of Neurite Outgrowth by SVG-TH Cells

As with the SVG cells, above, SVG-TH cells were also tested for their ability to promote neurite outgrowth and survival from either primary neurons or neuronal cell lines.

A. hNT Cell Line Cocultivation

A previously described cell line derived from a human teratocarcinoma was used in cocultivation experiments with SVG and SVG-TH cells. This cell line is derived from the parental teratocarcinoma cell line, by treatment of the parental cell line with retinoic acid and a combination of antimitotic agents. Upon treatment, the parental cell line will differentiate into post mitotic neurons. Andrews, P. W., Retinoic Acid Induces Neuronal Differentiation of a Cloned Human Embryonal Carcinoma Cell Line In Vitro, Dev. Biol. (1984) 103:285–293. These cells, termed hNT neurons, which were used in the cocultivation experiments described herein, retain many of the phenotypic qualities of neurons, including expression of neurofilament and secretion of neurotransmitters. Maintenance of these cells requires that they be plated on laminin or matrigel coated plates and that they be fed with conditioned media.

Figure 16A:
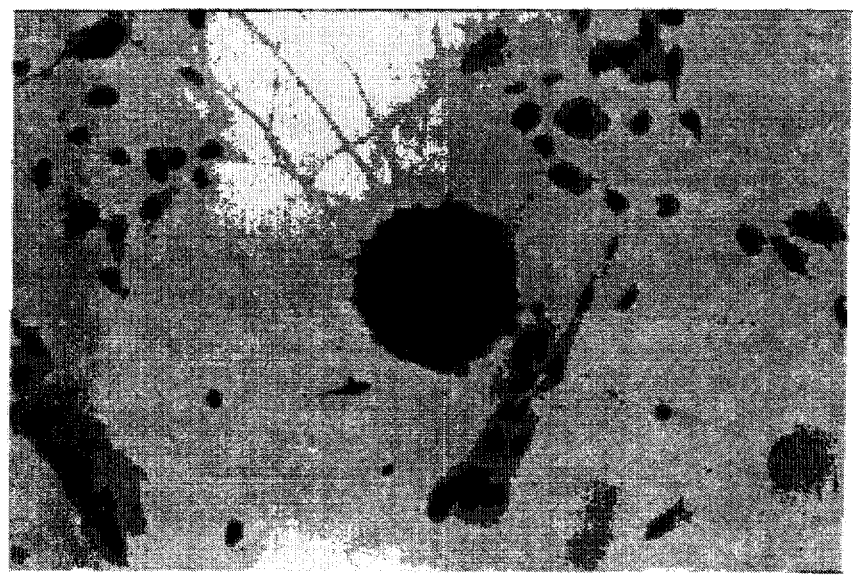
FIG. 16A shows immunohistochemical staining of cells from a hNT/SVG-TH cocultivation, after approximately 72 hours. The small flat individual cells are the SVG-TH cells.

In three separate experiments SVG, SVG-TH or Cos cells were plated in 6 well plates which had not been coated with any extracellular matrix (1×10⁵ cells per well). Forty-eight hours after the SVG, SVG-TH or Cos cells were plated, they were 30% confluent and 1×10⁵ hNT cells were plated into the same wells. The hNT cells were also plated into a fourth well which had none of the above three cell lines and which was not coated with an extracellular matrix. The cultures were fed only with D-MEM with 2% fetal calf serum. Twenty-four hours after plating, some of the hNT cells had attached to areas devoid of SVG and SVG-TH cells, and had also attached directly to these cells. There appeared to be roughly equal numbers of hNT cells and SVG or SVG-TH cells. Numerous small processes were seen on the hNT cells cocultivated with the SVG or SVG-TH cells. In the hNT/Cos cell cocultivation, the hNT cells had attached directly to the Cos cells, but were not found in areas devoid of Cos cells. Additionally, only about 1% of the Cos cells had hNT cells attached to them, and no processes were seen on the hNT cells. In the control dish, where the hNT cells were plated alone on an untreated surface, only a rare cell was seen to have attached. By seventy-two hours, the hNT cells had lifted up off the Cos cells and no hNT cells were found in the control dish. In contrast, the hNT cells in both the SVG and SVG-TH cocultivation had remained attached and sent out long processes which now had made contact with surrounding SVG/SVG-TH cells (FIG. 16A). Some of the cultures were fixed in acetone/methanol and immunohistochemistry for T protein was performed to unambiguously distinguish the two cell populations (FIG. 16A). These cultures remained viable for two weeks, after which the SVG and SVG-TH cells became confluent. The cocultures were passed into new plates and the same phenomena was seen again. After two more weeks, the experiments were terminated.

B. PC12 Cocultivation

Figure 16B:
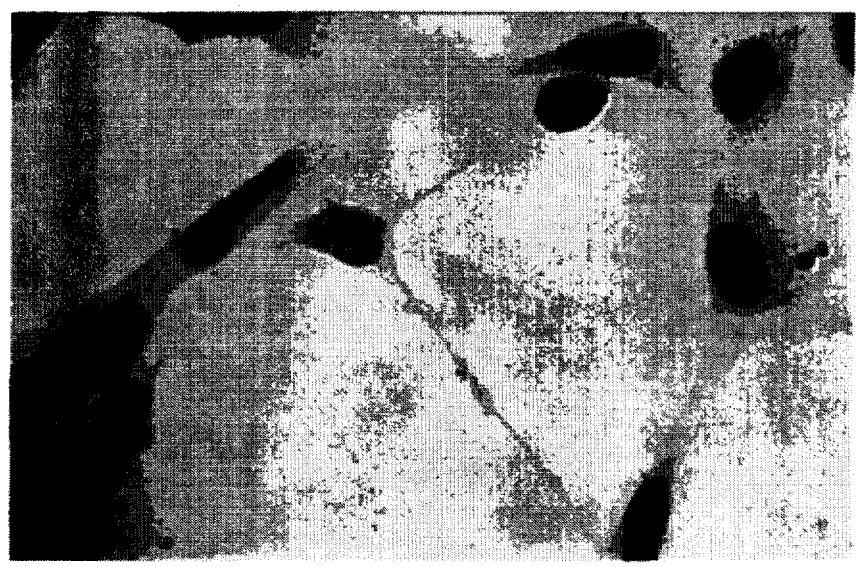
FIG. 16B shows immunohistochemical staining of cells from a PC12/SVG-TH cocultivation, after approximately 92 hours. A PC12 cell is shown near the center of the photograph with neuronal processes extending from it to the nearby SVG-TH cells. Similar results were obtained for SVG cells.

In this set of experiments, PC12 cells were cocultivated with either SVG, SVG-TH, Cos cells or plated alone. As in the hNT experiment, SVG, SVG-TH or Cos cells were plated into 6 well plates at 1×10⁵/well onto untreated plastic ware. Forty-eight hours later the PC12 cells were plated on all three cell lines as well as plated alone on untreated plastic. Forty-eight hours after cocultivation with either the SVG or SVG-TH cells, the PC-12 cells had attached to areas devoid of cells as well as directly onto the SVG and SVG-TH cells. The PC-12 cells had extended out neuritic processes which by ninety-two hours had made contact with surrounding SVG and SVG-TH cells. Some of the cultures were fixed in acetone and methanol and immunohistochemistry for T protein was performed to distinguish the two cell populations (FIG. 16B). After seventeen days the cultures became overgrown and the experiment was terminated. In contrast, PC12 cells cocultivated with Cos cells or cocultivated in isolation failed to extend out any processes.

In a separate set of experiments, PC12 cells were plated alone onto poly-d-lysine coated plates and then fed with unconditioned media or media conditioned from cultures of either SVG or SVG-TH cells. After seventy-two hours, the PC12 cells fed with conditioned media had developed neuritic processes, while those fed with unconditioned media did not change their morphology.

C. Primary Cultures of Fetal Rat Mesencephalic Neurons

To determine whether the SVG and/or SVG-TH cells could also support the survival of primary neurons, the mesencephalon from E13 fetal rats was dissected out, dissociated and plated in triplicate in 6 well plates. After twenty-four hours, a Costar transwell chamber was placed in the wells and either SVG or SVG-TH cells were passed into the transwell chamber (1×10⁵ cells). One set of mesencephalic cultures was not cocultivated with any cells to act as negative control. After seven days, the transwell chamber with the cells were removed and the mesencephalic cultures in the wells were fixed in acetone and methanol and stained by immunohistochemistry for tyrosine hydroxylase to determine the number of surviving mesencephalic neurons. As seen in FIG. 17, those mesencephalic cultures which were cocultivated with the SVG cells had two to threefold greater survival of tyrosine hydroxylase neurons relative to the control plate. Similar results were found with the SVG-TH cell line. No difference was seen in the morphology of the tyrosine hydroxylase positive neurons in either the control or cocultivation plates.

EXAMPLE 9

Engrafting and Identification of the SVG and SVG-TH Cells in the Rodent Striatum To determine if grafts of SVG or SVG-TH cells could be transplanted into the striatum and then unambiguously identified post transplantation, $5 \times 10^5$ cells, either SVG or SVG-TH, were engrafted into the striatum of Sprague Dawley rats using a stereotaxic head frame for the procedure. Ten animals were grafted with the SVG cells and ten were grafted with the SVG-TH cells. Either at three days or at seven days post-transplantation the animals were euthanized and the brain processed for immunohistochemistry. Five animals from both groups were perfused systemically with 4% paraformaldehyde at the time of euthanasia. Brain sections from the paraformaldehyde fixed animals were used for immunohistochemical staining with polyclonal antibodies, while the unfixed brain sections were used for immunohistochemical staining with monoclonal antibodies. The grafted SVG and SVG-TH cells in the striatum could be unambiguously differentiated from the surrounding parenchyma based on staining for SV40 T protein, which is only found in the grafted cells. Moreover, the grafted cells expressed the same antigens in vivo that they expressed in vitro, as confirmed by immunohistochemical staining. These include vimentin, serotonin, human MHC class I, T protein and TH. Similar to what was seen in vitro, only 40% of the SVG-TH cells were TH positive in vivo. The surrounding host parenchyma was also immunostained for vimentin and TH as well. The SVG-TH cells remained GFAP–, while the surrounding host parenchyma clearly has GFAP+ astrocytes. Staining for rat MHC class I stained the surrounding parenchymal blood vessels and the occasional host vessel seen in the graft, but failed to stain the grafted cells, as expected. An Electron microscopy study of the SVG-TH grafted cells found that the transplanted cells had retained the characteristic distended rough endoplasmic reticulum and coated vesicles, as was seen in FIG. 15. Similar results were obtained for SVG cells, with the exception that SVG cells were GFAP positive and TH negative.

EXAMPLE 10

Engrafting of the SVG and SVG-TH Cells into the Striatum of 6-hydroxydopamine Lesioned Sprague Dawley Rats Having determined that the SVG and SVG-TH cells could be identified in the striatum, the next object was to determine whether these cells could correct a functional deficit in an animal model of Parkinson's disease.

Figure 18:
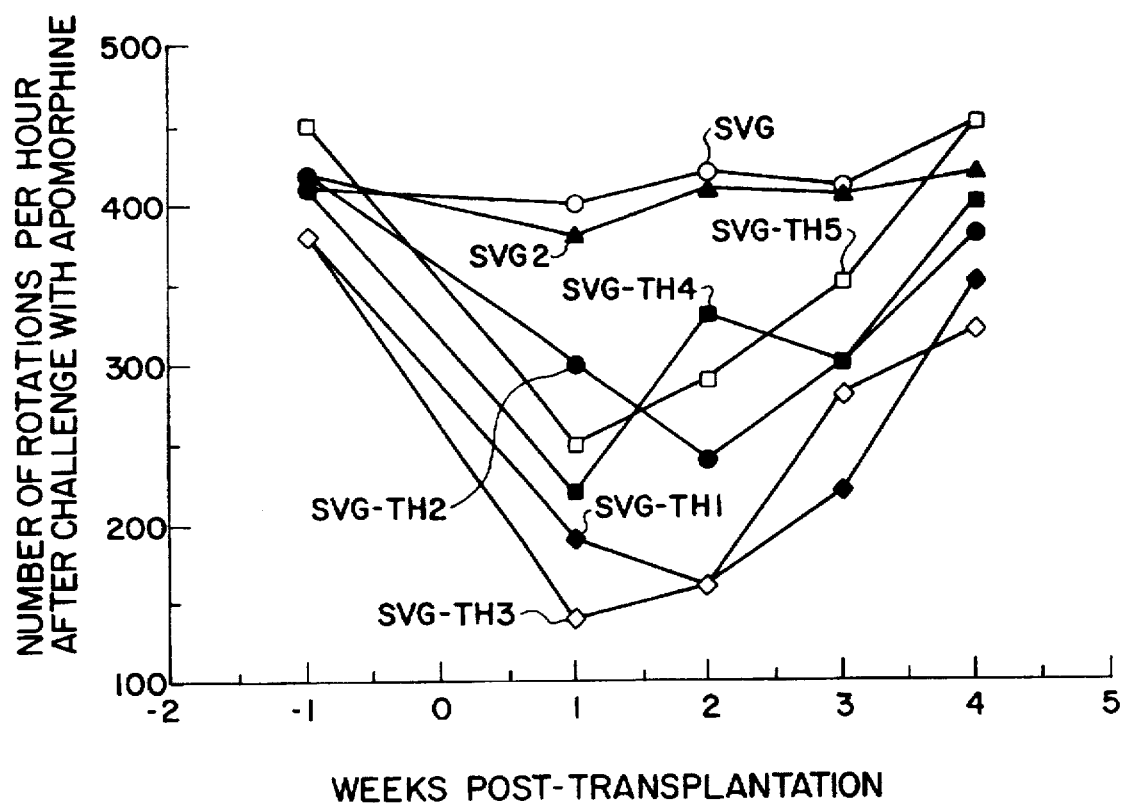
FIG. 18 shows the effect of SVG-TH transplantation in rat models of Parkinsonism. Functional deficit is indicated by the number of rotations per hour in the model rats. Shown is the number of rotations per hour after the rat was challenged with apomorphine, prior to and for 4 weeks following engrafting of SVG-TH cells into the lesioned striatum of the rats (shown as solid squares, solid diamonds, open squares, open diamonds and solid squares with clear dot). Also shown are results for two SVG transplantations (shown as solid triangles and open squares with black dot).

Seven Sprague Dawley rats underwent unilateral chemical lesioning of the substantia nigra with 6-hydroxydopamine using a stereotaxic head frame to direct the drug to the appropriate anatomical site. Five weeks post-lesioning, the animals were challenged with apomorphine to quantitate the degree of denervation. As seen in FIG. 18, all seven animals had baseline rotational rates of 400 revolutions/hour or more. Six weeks post-lesioning, five of the animals had SVG-TH cells (approx $5 \times 10^5$ cells) engrafted into the lesioned striatum. The two remaining animals had SVG cells engrafted into the striatum. At weekly intervals post-transplantation, for a total of four weeks, the animals were challenged with apomorphine to determine any change from their baseline activity. As seen in FIG. 18, one week post-transplantation, there was a substantial reduction in the amount of rotational behavior seen in the five animals grafted with the SVG-TH cells. In contrast, the animals grafted with the SVG cells showed some insignificant changes, as was expected given that these rats were completely denervated, lacking the ability to sprout dopaminergic neurons, and the SVG cells were unable to secrete L-dopa. Over the course of the next three weeks however, the animals grafted with the SVG-TH cells gradually returned to the pre-transplantation rotational behavior as seen in FIG. 18.

EXAMPLE 11

Characterization of the Engrafted Cells One Month Post-Transplantation

The seven 6 hydroxydopamine lesioned animals described in Example 10 above were euthanized one month post-transplantation. Three of the SVG-TH engrafted animals and one of the SVG engrafted animals were perfused systemically with 4% paraformaldehyde at the time of euthanasia. The remaining three animals were not perfused fixed at the time of euthanasia. Brain sections from the paraformaldehyde fixed animals were used for immunohistochemical staining with polyclonal antibodies, while the unfixed brain sections were used for immunohistochemical staining with monoclonal antibodies. The engrafted cells could still be identified one month post-transplantation by immunohistochemical staining for SV40 T protein, vimentin, serotonin and TH. However, the graft was significantly smaller than the grafts seen at day three or day seven post-transplantation. The graft was immunostained for large T protein, serotonin and vimentin; however, no TH immunostaining could be identified either in the graft or in the surrounding denervated striatum. The graft could further be identified by its lack of staining for rat Thy 1.1, an antigen strongly expressed in the surrounding host parenchyma. The host parenchyma demonstrated marked astrocytosis around the graft. When the sections were stained for rat CD4 and CD8, numerous positive cells were identified in and around the graft, suggesting that the graft was undergoing immunologic rejection. The above data indicates that the cells are a xenograft in the rodent CNS, whereas the survival of the cells in the primate CNS for upwards of nine months, reflects that these cells are allografts in that system.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be apparent that certain changes and modifications may be practiced within the scope of the appended claims.

What is claimed is:

1. A non tumorigenic and non inflammatory immortalized human neuro-glial cell line comprising a heterologous nucleic acid sequence which encodes a biologically active peptide, wherein said cell line is capable of 1) expressing said heterologous nucleic acid sequence and 2) inducing neuro migration or neurite extension in a mammal.

2. The cell line of claim 1, wherein said cell line is a glial cell line.

3. The cell line of claim 1, wherein said cell line is derived from human fetal astrocytes.

4. The cell line of claim 1, wherein said biologically active peptide is an enzyme.

5. The cell line of claim 1, wherein said biologically active peptide is a disease associated antigen.

6. The cell line of claim 1, wherein said biologically active peptide is tyrosine hydroxylase.

7. The cell line of claim 1, wherein said nucleic acid is operably linked to a transcriptional promoter.

8. The cell line of claim 6, wherein said cell line is an SVG-TH cell line.

9. The cell line of claim 6, wherein said cell line is capable of expressing the phTH/Neo plasmid.

10. The cell line of claim 1, wherein said cell line is further capable of expressing serotonin.

11. A transplantable composition, comprising:

cells from the cell line of claim 1; and a pharmaceutically acceptable carrier.

12. The transplantable composition of claim 11, wherein said cells are encapsulated by a membrane impermeable to antibodies.

13. The transplantable composition of claim 12, wherein said membrane is an alginate gel membrane.

14. A composition for promoting neurite outgrowth and survival comprising an immortalized human fetal neuro-glial cell line in an effective amount for promoting neurite outgrowth and survival in a pharmaceutically acceptable character.

15. The composition according to claim 14, wherein the immortalized human fetal neuro-glial cell line is further characterized by the following antigenic material: Vimetin, MHC Class I, and T protein.

16. The composition according to claim 14 wherein the immortalized human fetal neuro-glial cell line is SVG or SVG-TH.

17. The composition of claim 15, wherein the cell line expresses a heterologous protein.

18. The composition of claim 15 which further comprises in addition a cell line characterized by the expression of a neuro-filament and the secretion of neuro-transmitters.

19. The composition of claim 18, wherein the additional cell line is hNT or PC 12.

20. The composition according to claim 19 wherein the effective amount is 5 μl to 60 μl of a cell suspension having a cell density between about $10^4$ and $10^7$.

21. The immortalized human neuro-glial cell line of claim 1 further characterized as anchorage dependent, not capable of growth in soft augar, not exhibiting foci formation, and not expressing MHC Class II molecules.

22. The immortalized human neuro-glial cell line of claim 1 further characterized as a genetically modified derivative of an immortalized human neural fetal cell line identifiable as ATCC CRL 8621.

23. The immortalized human neuro-glial cell line of claim 1 wherein the biologically active peptide alleviates the symptoms of a neurological disorder characterized by a dopamine deficiency.

* * * * *